United States Patent [19]
Chin

[11] Patent Number: 5,718,703
[45] Date of Patent: Feb. 17, 1998

[54] METHOD AND APPARATUS FOR SMALL NEEDLE ELECTROCAUTERY

[75] Inventor: Albert K. Chin, Palo Alto, Calif.

[73] Assignee: Origin Medsystems, Inc., Menlo Park, Calif.

[21] Appl. No.: 404,120

[22] Filed: Mar. 14, 1995

Related U.S. Application Data

[63] Continuation of Ser. No. 123,130, Sep. 17, 1993, abandoned.

[51] Int. Cl.$^6$ .................................................. A61B 17/39
[52] U.S. Cl. ........................... 606/49; 606/50; 606/46; 606/52
[58] Field of Search .................... 606/41, 42, 45–52, 606/205–208; 607/100–102, 115, 116; 128/642

[56] References Cited

U.S. PATENT DOCUMENTS

| | | | |
|---|---|---|---|
| 1,943,543 | 1/1934 | McFadden | 606/49 |
| 2,022,065 | 11/1935 | Wappler | 606/49 |
| 4,003,380 | 1/1977 | Wien | 606/51 |
| 4,269,174 | 5/1981 | Adair . | |
| 4,418,692 | 12/1983 | Guay | 606/51 |
| 4,655,219 | 4/1987 | Petruzzi | 606/206 |
| 4,819,633 | 4/1989 | Bauer et al. | 606/52 |
| 4,920,982 | 5/1990 | Goldstein | 606/49 |
| 5,064,424 | 11/1991 | Bitrolf | 606/49 |
| 5,125,928 | 6/1992 | Parins et al. | 606/48 |
| 5,269,780 | 12/1993 | Roos | 606/50 |
| 5,318,564 | 6/1994 | Eggers | 606/5 |
| 5,415,656 | 5/1995 | Tihon et al. | 606/47 |
| 5,501,654 | 3/1996 | Failla et al. | 606/47 |

FOREIGN PATENT DOCUMENTS

| | | | |
|---|---|---|---|
| 2325626 | 11/1974 | Germany | 606/51 |

OTHER PUBLICATIONS

Medical Tribune News Service Article: "Vasectomy Without Scalpels".

Primary Examiner—Michael Peffley
Attorney, Agent, or Firm—Limbach & Limbach L.L.P.

[57] ABSTRACT

An apparatus and method for cauterizing small vessels through small incisions or puncture openings is described. The apparatus is comprised of a pair of elongate electrodes capable of being inserted into a hollow needle. In a preferred embodiment, the elongate electrodes are disposed within a tube that is slidable in a longitudinal direction between a proximal position, in which the tube releases the electrodes into an outwardly biased position, and a distal position in which the electrodes are enclosed by the tube. The device is introduced into a body cavity with the tube in the distal position. The tube is then moved to its proximal position to release the electrodes, and a vessel is grasped using hooks at the electrode tips. A different electrical polarity is applied to each electrode, causing current to pass through the vessel from one electrode to the other to cauterize the vessel.

3 Claims, 6 Drawing Sheets

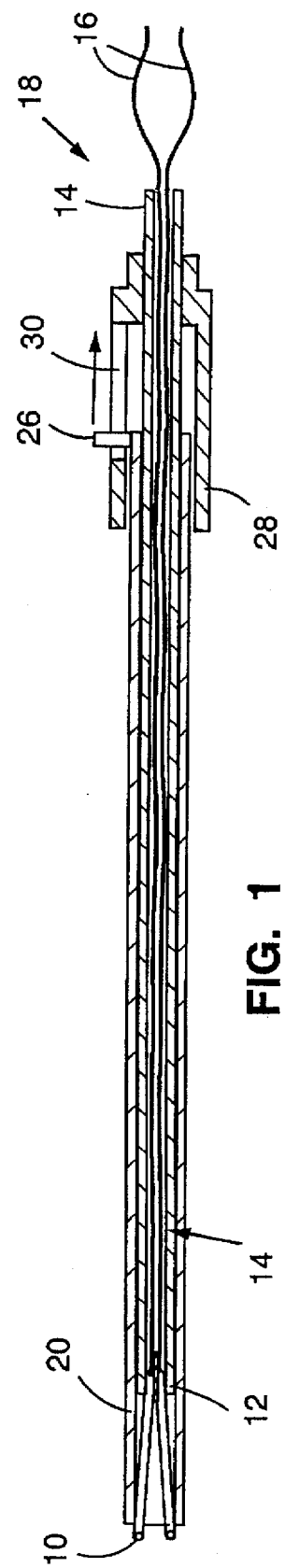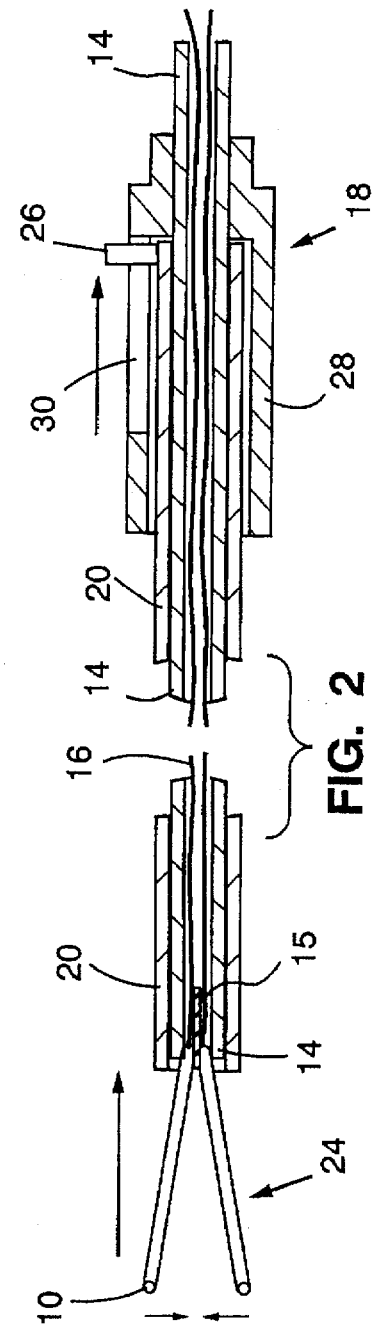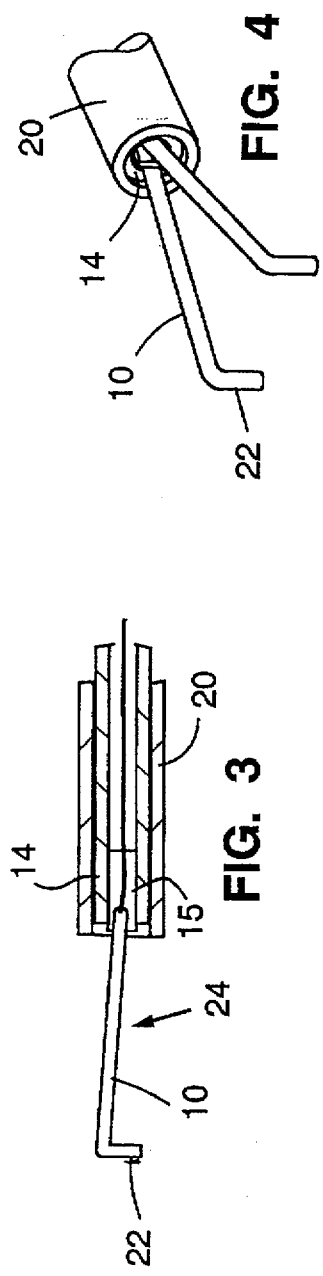

METHOD AND APPARATUS FOR SMALL NEEDLE ELECTROCAUTERY

This is a continuation of application Ser. No. 08/123,130 filed on Sep. 17, 1993 (now abandoned).

FIELD OF THE INVENTION

The present invention relates to a method and apparatus for performing electrocautery using instruments inserted through small diameter puncture needles, trocars, or small incisions.

BACKGROUND OF THE INVENTION

Electrocautery is a method for destroying tissue by passing electrical current through it. Some medical procedures require cauterization of certain vessels in order to permanently prevent the passage of blood or other substances through those vessels. In gallbladder surgery, isolation of the gallbladder often requires cauterization of the cystic artery, the artery which carries blood to the gallbladder. Cauterization of the vessels in the mesentery, the fold attaching the bowel to the body wall, is needed during bowel resection to provide surgical access to the bowel. Cauterization is also frequently used to seal the vas deferens in vasectomy, and in tubal ligation to seal the fallopian tubes to block the passage of sperm and egg, respectively.

With existing electrocautery devices, access to the vessels to be sealed is gained through incisions. The vessels sought to be cauterized are often grasped with surgical instruments inserted into the incision and pulled into the open where they are cauterized.

In light of recent trends towards minimizing recovery patient time, existing electrocautery devices are often inconvenient because their use can require incisions which necessitate longer periods of recovery. Existing electrocautery devices are used through trocar openings, which provide access to the thoracic and abdominal cavities through 5–10 mm puncture openings for laparoscopic procedures. Even these relatively small trocar punctures are not feasible for providing access to the vas deferens in vasectomy because of the potential risk that surrounding structures will be damaged. Use of approximately 10 mm incisions has continued in these sterilization procedures, continuing the need for recovery periods of up to two weeks.

OBJECTS AND SUMMARY OF THE INVENTION

It is an object of the present invention to provide a device capable of being inserted through a small opening and used to isolate and electrocauterize vessels and ducts (collectively referred to herein as "vessels").

The present invention provides one or more elongate electrodes which are capable of being inserted through a small incision, laparoscopic trocar, hollow needle or needle puncture, and a means for applying an electrical potential across the electrodes. The electrodes may be confined by a sliding tube during insertion in order to prevent the electrodes from snagging on body tissue. The electrodes may also have hooking means on their ends to enable hooking of the vessels sought to be isolated.

DESCRIPTION OF THE DRAWINGS

FIG. 1 is a side sectional view of the preferred electrocauterization device according to the invention.

FIG. 2 is a partial side sectional view of the preferred electrocauterization device of FIG. 1 showing the sliding tube in a proximal position.

FIG. 3 is a partial side sectional view of the preferred electrocauterization device if FIG. 1 showing a hook at the distal tip of an electrode.

FIG. 4 is a perspective view of the distal end of the preferred electrocauterization device of FIG. 1.

DETAILED DESCRIPTION OF THE INVENTION

Figure 5A:
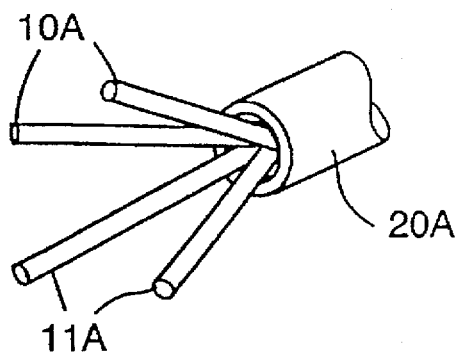
FIG. 5A is a perspective view of the distal end of a first alternative embodiment of an electrocauterization device according to the invention.

The preferred embodiment of the present invention is generally comprised of spring biased elongate electrodes 10 which extend from the distal end 12 of an elongate tubular shaft 14. Electrode leads 16 extend from the proximal end 18 of the elongate shaft 14, and a tube 20 is slidably disposed around the electrodes 10 and the shaft 14.

Referring to FIG. 2, the distal cauterization ends 24 of the electrodes 10 extend through the shaft 14 and are secured to the shaft at its distal end 12. The electrodes 10 are electrically conductive wires and are spring biased at their cauterization ends 24 to normally extend laterally of each other, away from the longitudinal axis of the shaft as shown in FIG. 2. A hook 22 (see FIG. 4) is formed at the distal end of each cauterization end 24. The electrodes are covered by an insulating material, except for their hooks 22 and cauterization ends 24.

The tube 20 is slidable in the longitudinal direction around the shaft 14 and the electrodes 10. In the distally extended position shown in FIG. 1, the tube 20 confines the cauterization ends 24 of the electrodes 10 to a generally axial orientation. In the retracted proximal position of the tube shown in FIG. 2, the cauterization end 24 of each electrode extends from the distal end of the tube 20 and the cauterization ends 24 are in their laterally biased position. A finger tab 26 is fixed to and protrudes laterally from the proximal portion of the tube 20.

A tubular handle 28 is disposed around the proximal end of the tube 20 and the proximal portion of the shaft 14. The handle 28 is secured to the shaft 14, but is loosely situated around the tube 20 to allow the tube to slide in the longitudinal direction. The finger tab 26 protruding from the tube 20 extends through an elongate slot 30 in the handle 28. The slot 30 is sufficiently long to allow the tube 20 to be translated between its proximal and distal positions by sliding the finger tab 26 in the slot 30.

Prior to use, the finger tab 26 is advanced in the distal direction to slide the tube 20 around the cauterization ends 24 of the electrodes 10. The distal end of the instrument is next inserted into a body cavity through a trocar, hollow needle, or small incision. The tube 20 is withdrawn to its proximal position, and the hooks 22 are then used to lift a vessel away from surrounding tissue. Each of the two electrode leads 16 is connected to a power source and is maintained at a different electrical potential, with one lead maintained at a positive polarity and the other lead maintained at a negative polarity. When engaged with a vessel, current passes through the vessel from one electrode to the other, causing the section of vessel lying between the hooks to heat and produce cauterized tissue. The cauterized tissue prevents fluid from passing through the vessel. The cauterized section of the vessel may be severed with a scalpel, and sutures may be applied to each severed end of the vessel.

The apparatus may alternately be used in monopolar fashion by grounding the patient using conventional means, such as a grounding pad adhered to the patient's skin, and by maintaining both electrodes at the same polarity.

Figure 5B:
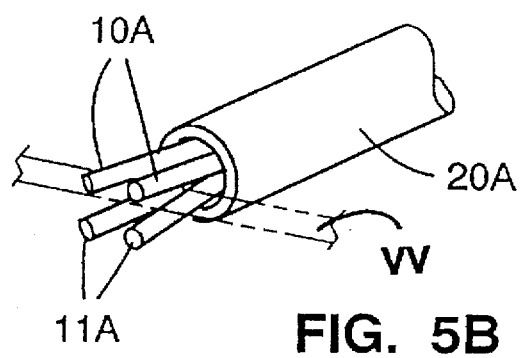
FIG. 5B is a perspective view of the distal end of the first alternative embodiment of FIG. 5A showing the cauterization ends of the electrodes clamped around a vessel.

The first alternative embodiment, shown in FIG. 5A, has two pairs of elongate electrodes 10A, 11A. During use, a vessel VV is positioned between the first pair 10A and the second pair 11A of electrodes. When the tube 20A is moved from its proximal position to its distal position, the first pair 10A of electrodes and the second pair 11A of electrodes are pushed towards each other and thereby clamp down on the vessel VV positioned between them as shown in FIG. 5B. For bipolar use, two of the electrodes are maintained at a first electrical potential having positive polarity and the other is maintained at a second electrical potential having negative polarity. For monopolar use, the patient is grounded as described above and all of the electrodes are maintained at a single electrical potential.

Figure 5C:
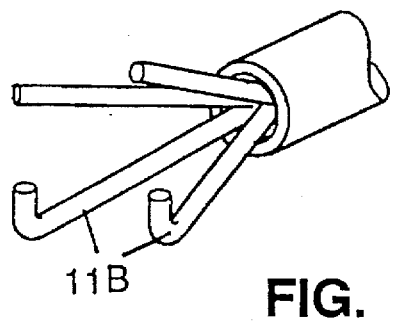
FIG. 5C is a perspective view of the distal end of a second alternative embodiment of an electrocauterization device according to the invention.

As shown in FIG. 5C, one pair 11B of electrodes for the first alternative embodiment may be formed into hooks at their distal ends so as to enable separation of the vessel from surrounding tissue during use.

Figure 6A:
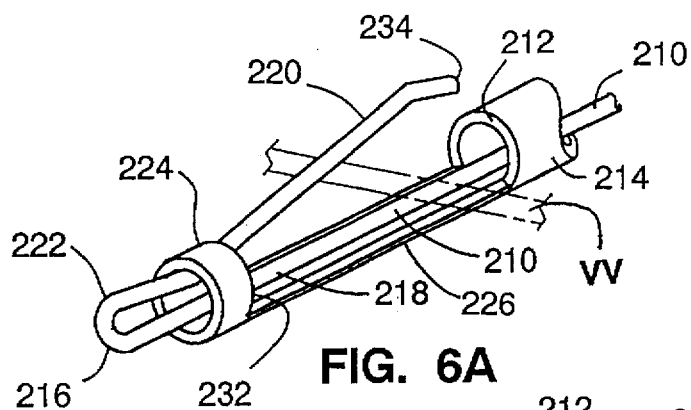
FIGS. 6A and 6B are perspective views of the distal end of a third alternative embodiment of an electrocauterization device according to the invention showing the electrode in the open and closed position, respectively.
Figure 6B:
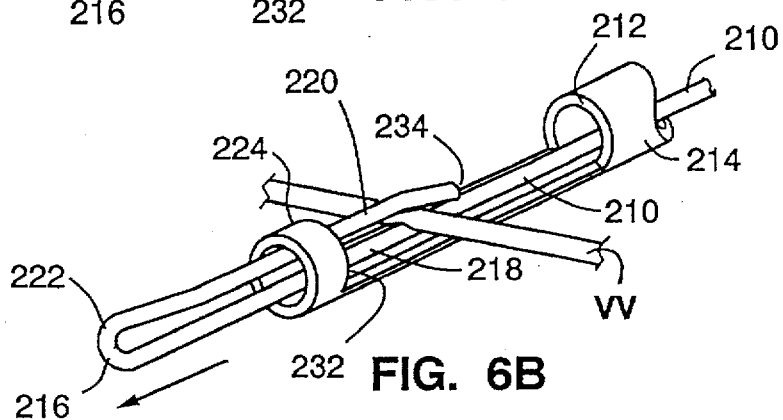

The distal portion of a third alternative embodiment is shown in FIGS. 6A and 6B. The third alternative embodiment is comprised of a single electrode 210 extending from the distal end 212 of an elongate tubular shaft 214. The electrode 210 is slidable within the elongate tube in a longitudinal direction.

The distal end 216 of the electrode 210 is folded such that the electrode 210 has a first straight portion 218 and a second straight portion 220 joined at an elbow 222. The second straight portion 220 is biased away from the first straight portion 218 such that the proximal end 234 of the second straight portion is spaced from the first straight portion 218 when the second straight portion 220 is in its resting position as shown in FIG. 6A.

A short tubular sleeve 224 having a throughbore 232 is connected by a member 226 to the distal end 212 of the elongate tubular shaft 214. A portion of the electrode 210 is positioned within the throughbore 232 with the elbow 222 positioned distally of the tubular sleeve 224 and the proximal end 234 of the second straight portion 220 of the electrode positioned proximally of the tubular sleeve 224.

The electrode 210 is slidable in a longitudinal direction within the elongate tube. When the electrode 210 is in a proximal position, shown in FIG. 6A, the second straight portion 220 of the electrode 210 is in its resting position. Advancing the electrode 210 to a distal position, as shown by an arrow in FIG. 6B, causes the electrode to advance distally within the tubular sleeve 224. As the electrode advances in the distal direction, the second straight portion 220 is constricted by the tubular sleeve 224 causing its proximal end 234 to move laterally towards the first straight portion 218.

The third alternative embodiment is operable in monopolar fashion. Prior to use, a grounding electrode (not shown) is connected to the patient. A vessel VV is then positioned between the first and second straight portions of the electrode as shown in FIG. 6A. The electrode 210 is advanced in a distal direction causing lateral movement of the second straight portion 220 as the electrode 210 passes through tubular sleeve 224 and thus causing the vessel VV to be clamped between the first 218 and second 220 straight portions of the electrode. Once a vessel VV is clamped between the first 218 and second 220 straight portions of the electrode 212, current is delivered to the electrode 210.

Figure 7A:
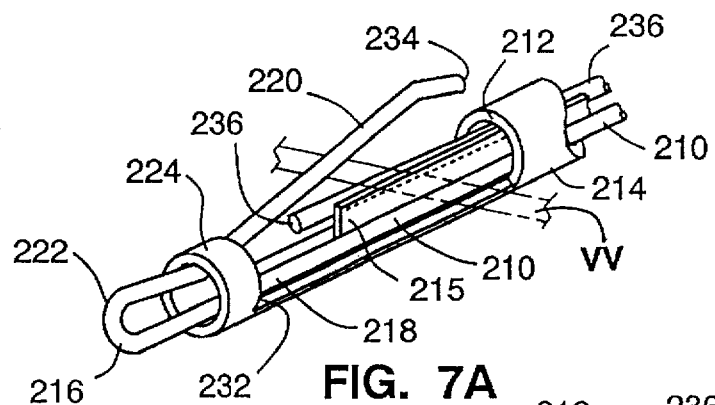
FIGS. 7A and 7B are perspective views of the distal end of a fourth alternative embodiment of the electrocauterization device according to the invention.
Figure 7B:
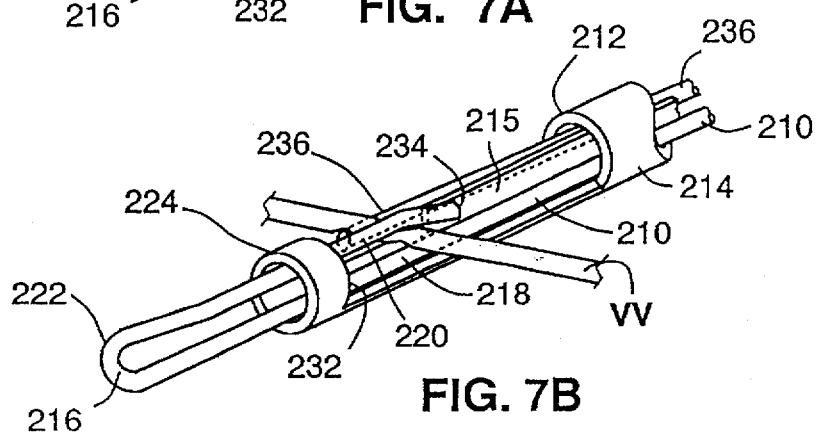

In a fourth alternative embodiment, shown in FIGS. 7A and 7B, a device similar to the third alternative embodiment is configured for bi-polar use by adding a second electrode 236 parallel to the first straight portion 118 of electrode 210 but electrically insulated from it by insulating material 215. When a vessel VV is clamped between the first 218 and second 220 straight portions of electrode 210, it makes contact with the both the first and second electrodes 210, 236. Current is delivered to both the first and second electrodes, with each electrode receiving current of an opposite polarity.

While the apparatus of the present invention may be used during a variety of surgical procedures, it is particularly useful for performing vasectomies. The method of using the apparatus of the preferred embodiment to perform a vasectomy will next be described.

EXAMPLE

Vasectomy involves removing a section of the vas deferens, a pair of tubular channels through which sperm passes from the testicles to the penis. In a conventional vasectomy, a 10–15 mm long incision is made on one side of the scrotum. The vas deferens is identified and pulled up into the incision. A scalpel is used to sever out a 10–15 mm segment of the vas deferens. The segment is removed and the remaining ends are cauterized. A loop of suture is tied around each remaining end to prevent sperm from exiting the vas during healing. The incision is sutured and the procedure is repeated through a second incision made on the opposite side of the scrotum.

Using the apparatus and method of the present invention, vasectomies may be performed through small needles rather than incisions. FIG. 9 shows the instruments required for performing a small needle vasectomy using the present invention. FIGS. 8A through 8H illustrate the steps for performing the vasectomy.

Figure 8A:
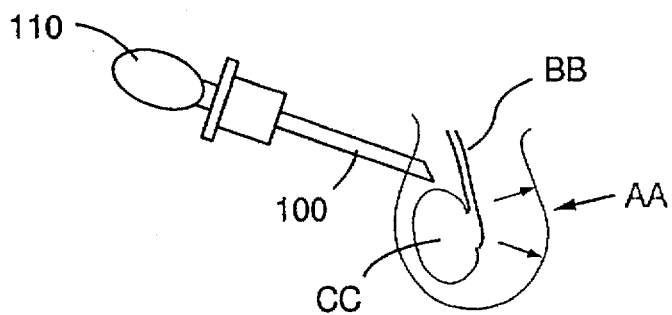
FIGS. 8A through 8H are schematic representations showing the series of steps for performing a vasectomy according to the present invention.
Figure 8B:
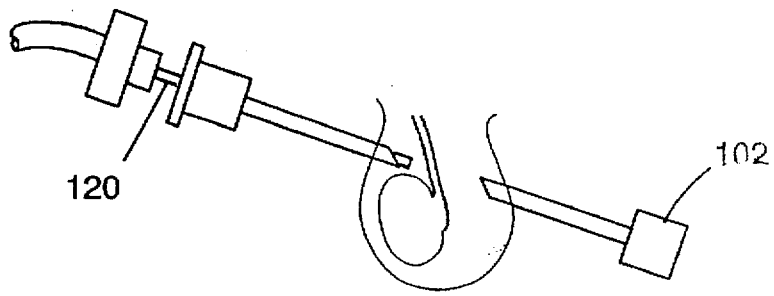
Figure 8C:
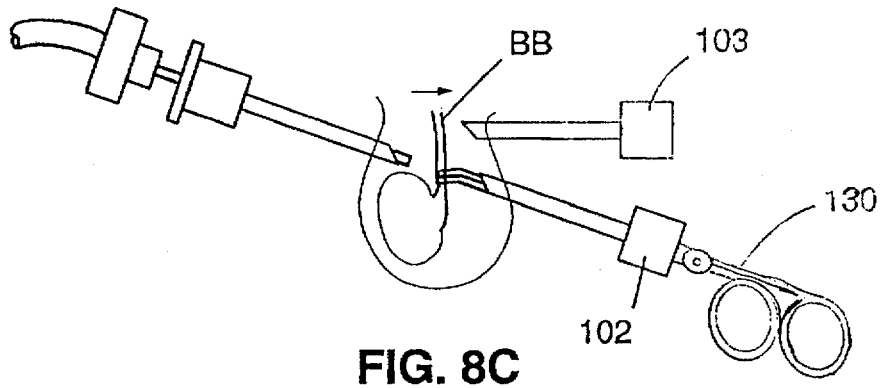
Figure 9:
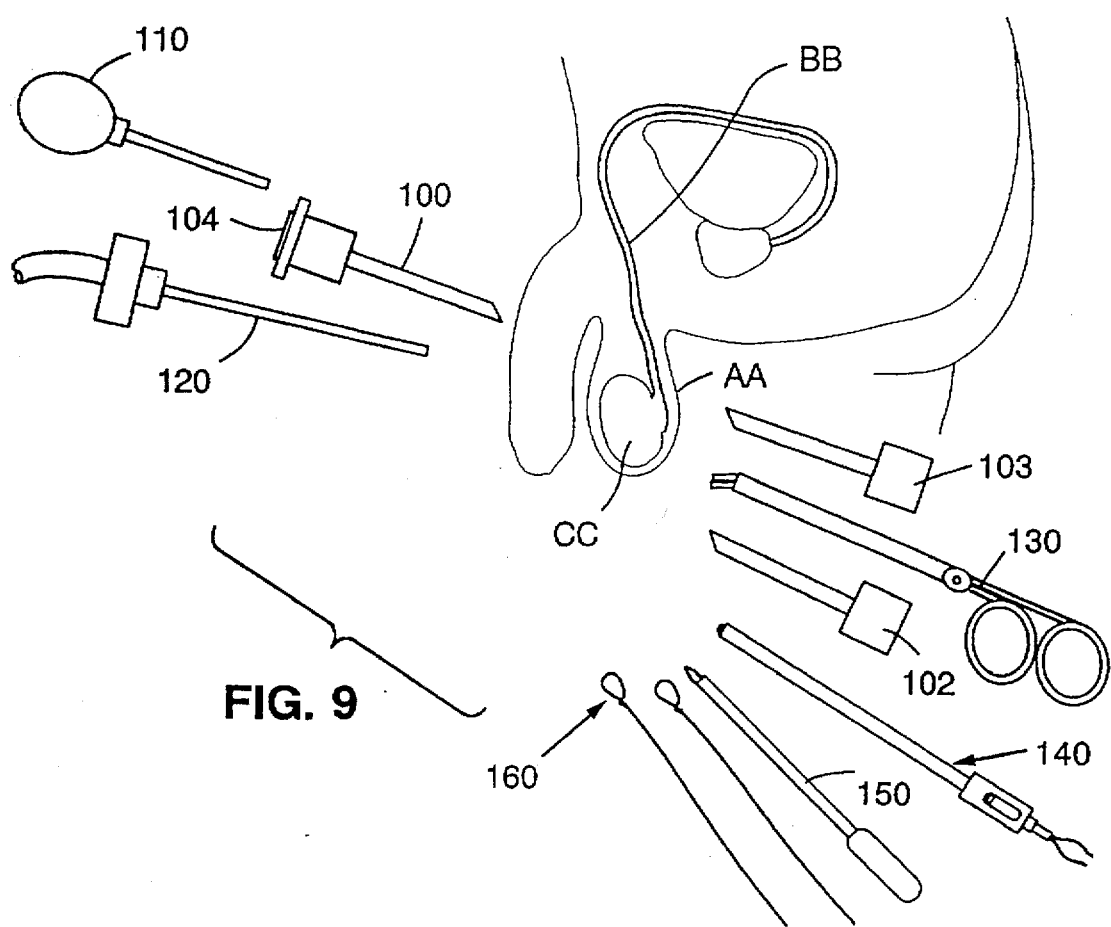
FIG. 9 is a schematic representation of the male reproductive anatomy and instruments necessary for performing a vasectomy according to the present invention.

Referring to FIG. 8A, a hollow 14 gauge needle 100 is inserted into the scrotum AA and approximately 15–20 cc of insufflation air or carbon dioxide is delivered through the needle using a syringe or a squeeze bulb 110 having a one-way valve. Insufflation provides visualization and working space within the scrotum. The needle 100 should have a sealing mechanism, such as a septum sealing cap 104, to prevent loss of air or carbon dioxide from the insufflated scrotum when the syringe is removed.

After removal of the syringe, a fiberoptic scope 120 is inserted through the sealing cap 104 to enable visualization of the vas deferens BB and the testicle CC. Two additional hollow needles 102, 103, also having sealing means, are next introduced into the scrotum AA. A grasper 130 is then passed into the scrotum AA through the needle 102 and is used to grasp the vas deferens BB.

Figure 8D:
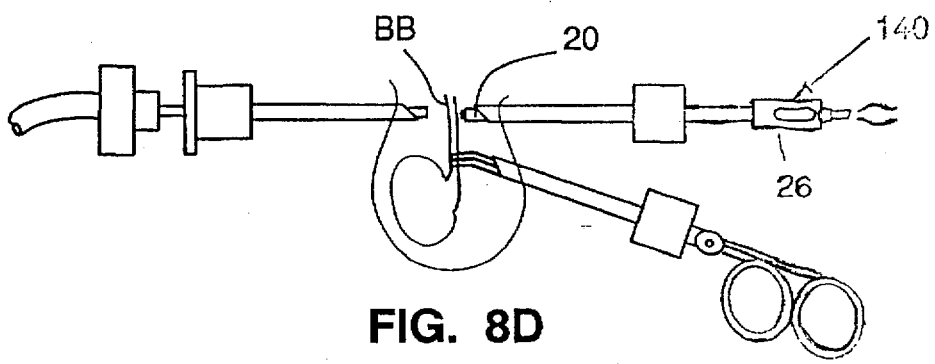
Figure 8E:
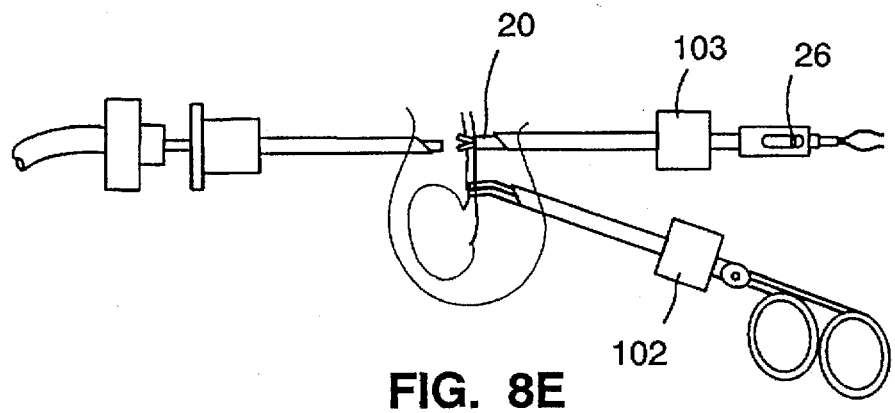

A small needle cauterization device 140 is next passed through needle 103 with the slidable tube 20 in its distal position as shown in FIG. 8D. The electrodes are next exposed by sliding the finger tab 26 in the proximal direction to withdraw the slidable tube to its proximal position, as in FIG. 8E. The hooks (not shown) at the distal ends of the electrodes are hooked around the vas deferens, and the vessel is cauterized as described above.

Figure 8F:
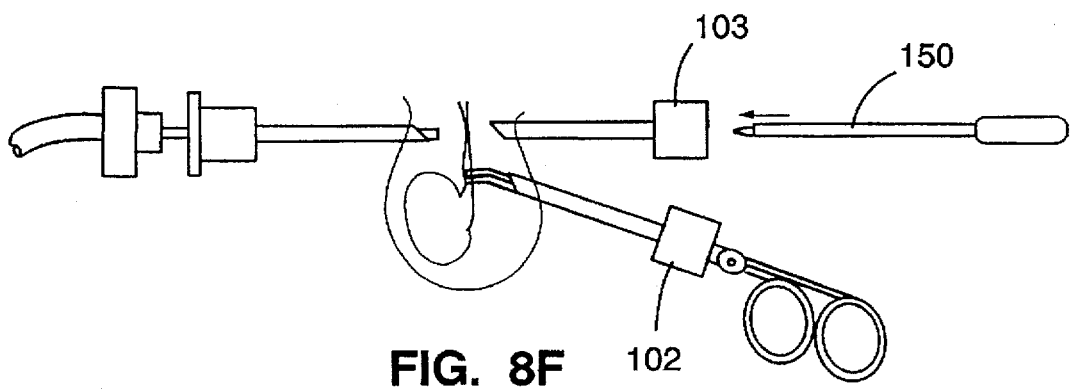
Figure 8G:
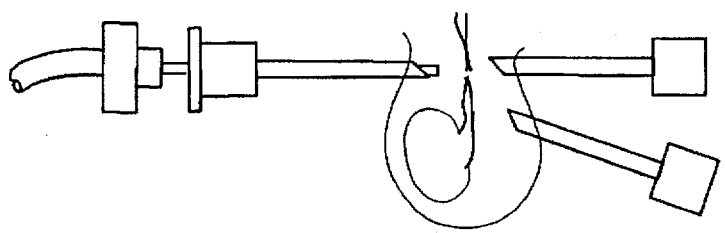
Figure 8H:
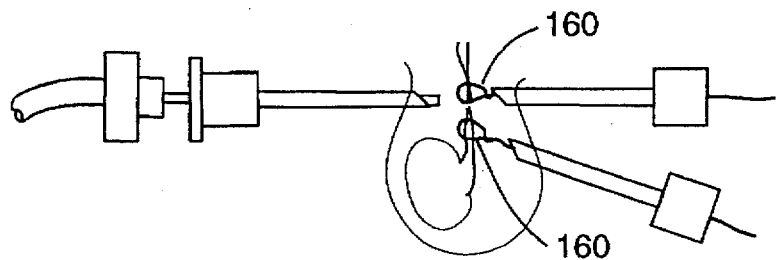

The cauterization device is next withdrawn from the needle 103 and a scalpel 150 is inserted through the needle as shown in FIG. 8F and used to sever the cauterized portion of the vas deferens. As with the conventional procedure, two small suture loops 160 are tied around the severed ends of the vas deferens. As shown in FIGS. 8G and 8H, the grasper 130 and the scalpel 150 are next withdrawn, and two small suture loops 160 are tied around the severed ends of the vas deferens.

CONCLUSION

A number of embodiments of the apparatus of the present invention and one procedure for using the present invention have been described. However, many other embodiments and procedures exist which fall within the scope of the present invention. The scope of the invention is not intended to be limited by the embodiments described, but is limited only as set forth in the appended claims.

I claim:

1. An electrocautery apparatus comprising:

a handle;

a first elongate electrode having a first section extending from the handle, and a second section folded back over the first section so as to dispose the first and second section in spaced laterial relationship, the second section having a free end spaced and detached from the handle and the first section of the electrode; and an actuator containing the first elongate electrode, at least one of the actuator and the elongate electrode being slidable relative to the other for moving at least one of the first and second sections towards the other of the first and second sections to selectively adjust the relative laterial separation of the first and second sections of the elongate electrode to engage opposite sides of a vessel to be cauterized therebetween the actuator containing the first and second sections in a lateral relationship.

2. The apparatus of claim 1 further comprising:

a second elongate electrode extending from the handle and positioned adjacent to the first section of the first elongate electrode; and insulating means insulating the first elongate electrode from the second elongate electrode.

3. The apparatus of claim 1 wherein the actuating means includes a tube disposed around first and second sections of the electrode and slidable between a distal position, wherein the first and second sections are spaced by a first distance, and a proximal position, wherein the second section is urged towards the first section by the tube such that the first and second sections are spaced by a second distance, the second distance being shorter than the first distance.

* * * * *

UNITED STATES PATENT AND TRADEMARK OFFICE
CERTIFICATE OF CORRECTION

PATENT NO.   : 5,718,703
DATED        : February 17, 1998
INVENTOR(S)  : Albert K. Chin, M.D.

It is certified that error appears in the above-indentified patent and that said Letters Patent is hereby corrected as shown below:

Column 6, line 4, delete "section" and insert therefor --sections--.

Column 6, lines 4 and 12, delete "laterial" and insert therefor--lateral--.

Signed and Sealed this

Thirtieth Day of June, 1998

Attest:

BRUCE LEHMAN

Attesting Officer

Commissioner of Patents and Trademarks